(12) United States Patent
Ahrens

(10) Patent No.: US 9,370,614 B2
(45) Date of Patent: Jun. 21, 2016

(54) RECIRCULATION DETECTION BY ADMINISTRATION OF A BOLUS

(71) Applicant: B. BRAUN AVITUM AG, Melsungen (DE)

(72) Inventor: Joern Ahrens, Baunatal (DE)

(73) Assignee: B. BRAUN AVITUM AG, Melsungen (DE)

( * ) Notice: Subject to any disclaimer, the term of this patent is extended or adjusted under 35 U.S.C. 154(b) by 165 days.

(21) Appl. No.: 14/217,991

(22) Filed: Mar. 18, 2014

(65) Prior Publication Data

US 2014/0291534 A1  Oct. 2, 2014

(30) Foreign Application Priority Data

Mar. 28, 2013  (DE) .................. 10 2013 103 222

(51) Int. Cl.
  *A61M 1/16*   (2006.01)
  *A61M 1/36*   (2006.01)
  *G01N 21/59*  (2006.01)

(52) U.S. Cl.
  CPC ........... *A61M 1/1694* (2013.01); *A61M 1/1617* (2014.02); *A61M 1/3664* (2013.01); *G01N 21/59* (2013.01); *A61M 2205/3313* (2013.01)

(58) Field of Classification Search
  CPC ........................................................ A61M 1/16
  See application file for complete search history.

(56) References Cited

U.S. PATENT DOCUMENTS

| | | |
|---|---|---|
| 5,685,989 A | 11/1997 | Krivitski et al. |
| 6,156,002 A | 12/2000 | Polaschegg et al. |
| 6,666,840 B1 | 12/2003 | Falkvall et al. |
| 6,702,774 B1 | 3/2004 | Polaschegg |
| 7,172,570 B2 * | 2/2007 | Cavalcanti .......... A61M 1/3621 210/645 |
| 7,815,852 B2 * | 10/2010 | Sternby ................ A61B 5/0275 210/321.71 |
| 2006/0096348 A1 | 5/2006 | Difiore |
| 2008/0149563 A1 * | 6/2008 | Ash .......................... A61M 1/16 210/646 |

(Continued)

FOREIGN PATENT DOCUMENTS

| | | |
|---|---|---|
| DE | 197 47 360 | 4/1999 |
| DE | 699 16 053 | 3/2005 |
| DE | 10 2007 056 475 | 6/2009 |

(Continued)

OTHER PUBLICATIONS

German Search Report for DE 10 2013 103 222.2 issued Dec. 6, 2013.

(Continued)

*Primary Examiner* — Casey Bryant
(74) *Attorney, Agent, or Firm* — RatnerPrestia

(57) ABSTRACT

Methods and devices implementing, for detecting a recirculation, at the side of a dialysis solution, by a blood-sided administration of a bolus are disclosed. Recirculation may be detected by: measuring a first light absorbance value (ad) of a dialysis solution (d) draining off a dialyzer using a spectrometer, prior to the administration of the bolus; venous administration of the bolus having a predefined volume (QBven) at the venous access; measuring a second light absorbance value (bd) of the draining dialysis solution using a spectrometer, after the administration of the bolus; and determining a change in the absorbance value between the first (ad) and second (bd) measured absorbance values due to the presence of a bolus in the dialysis solution during recirculation as a basis for the recirculation quantification.

7 Claims, 5 Drawing Sheets

(56) References Cited

U.S. PATENT DOCUMENTS

| | | |
|---|---|---|
| 2011/0004141 A1 | 1/2011 | Zhang et al. |
| 2012/0298581 A1 | 11/2012 | Wehmeyer et al. |

FOREIGN PATENT DOCUMENTS

| | | |
|---|---|---|
| DE | 10 2011 008482 | 1/2012 |
| DE | 10 2011 102 962 | 11/2012 |
| EE | DE 102011008482 A1 * | 1/2012 .............. A61M 1/16 |
| EP | 0 900 094 | 3/1999 |
| EP | 2 292 283 | 3/2011 |
| WO | WO 98/32477 | 7/1998 |

OTHER PUBLICATIONS

Extended European Search Report for EP 14157989.6-1662 mailed Jul. 4, 2014.

* cited by examiner

RECIRCULATION DETECTION BY ADMINISTRATION OF A BOLUS

CROSS REFERENCE TO RELATED APPLICATIONS

This application claims priority to German application DE 10 2013 103 222.2 filed Mar. 28, 2013, the contents of such application being incorporated by reference herein.

FIELD OF THE INVENTION

The present invention relates to a (control) method as well as to a device for a machine-internal detection of a recirculation state by/during the administration of a bolus.

BACKGROUND OF THE INVENTION

The dialysis is a blood purification method which is used as a substitution method in case of renal failure. Apart from a kidney transplant, dialysis is the only and thus most important renal substitution therapy in case of chronic renal failure and one of the treatment options for acute renal failure. The term "dialysis" is to be understood as an exchange of substances through a membrane, with blood/plasma being present on the one membrane side and a dialysis solution being present on the other side of the membrane or flowing along it according to the countercurrent principle.

During a treatment, blood is pumped out of the patient via a patient-side access, is conveyed past the dialysis membrane in the dialyzer (filter) and returned to the patient in cleaned condition. In a hemodialysis or hemodiafiltration mode of the dialysis apparatus, any poisonous substances and uremic toxins (metabolic degradation products) and low-molecular substances (which are able to penetrate the membrane) are transported from the blood by concentration gradients (diffusion) and/or ultrafiltration (convection) via the membrane to the other filter side into the dialysis solution and are removed in this way. There is a constant flow of fresh dialysis solution through the dialyzer (approximately 500 ml/min).

Usually, the hemodialysis treatment is carried out for approximately 4 to 5 hours (dialysis overnight up to 8 hours) for every treatment and at least three times a week (depending on the body weight, renal residual function, cardiac output).

Patients who perform the hemodialysis at home avoid the problematic, longer treatment interval at the weekend and carry out the dialysis more frequently, as a rule every second day or even daily.

An important factor of influence on the quality of the dialysis is the blood flow. Generally speaking, the higher the blood flow, the better the result of the treatment. However, it may happen that problems occur in the dialysis shunt implanted in the patient used for taking blood and returning it, in particular if the blood flow is high in the extracorporeal system. The specific level of the blood flow at which these problems will occur depends on the quality of the patient-side access and on the blood flow through the shunt as well as its integrity (no stenosis or aneurysm).

During the dialysis, a so-called recirculation may occur in the shunt due to a change in the access, because of stenosis or if the flow in the shunt is too low. A recirculation causes the direct backflow of cleaned blood from the venous access directly into the arterial access of the dialyzer, whereby the effectiveness of the dialysis is significantly reduced. This is why it should/must be ensured that the dialysis performance does not decrease during the entire therapy and thereby an effective dialysis can be guaranteed.

In order to detect a recirculation in the shunt during the dialysis treatment, there already exist various control methods in prior art which are performed on the patient independently of the medical dialysis treatment method, the principles being illustrated in the following sections.

DESCRIPTION OF THE RELATED ART

Accordingly, the determination of a recirculation in the shunt of the patient is already presented in prior art by various methods. In some of the dialysis apparatus which are known per se, the identification of the recirculation is realized for instance by a temperature check performed via sensor technology (EP 0 900 094). To this end, the blood conducted outside the body is provided with a bolus in the form of a temperature pulse in the venous line portion. The measurement of temperature in the arterial line portion or system allows conclusions to be drawn as to the percentage of the recirculation on the basis of a temperature change.

Further, the respective prior art offers a measurement of the inline dialysis, performed on the basis of a measurement of the conductivity and likewise operating with the administration of a suitable bolus. Here, the recirculation in the shunt of a dialysis patient is determined by measuring the conductivity. With this method, too, an electrolyte bolus which modifies the conductivity of the liquid is administered by means of the dialysis solution to the venous hose portion. Due to the determination of the conductivity in the dialysis solution outflow downstream of the dialyzer, conclusions can be drawn as to the level of the recirculation (internal to the machine) (U.S. Pat. No. 7,815,852).

Moreover, a recirculation may basically also be determined by means of a hematocrit sensor. In doing so, the hematocrit of the blood is changed by administering a defined bolus to the venous line portion. The determination of the hematocrit in the arterial line system allows for the detection of recirculation. Technical proposals which are based on this principle are disclosed, for instance, in U.S. Pat. No. 5,685,989. These known products are based either on the measurement of the recirculation by means of electromagnetic radiation in the visible range, or on the measurement of the recirculation by ultrasound.

The described methods and products are able to determine the recirculation in the patient-side access in different ways. It is explicitly referred to the fact that the methods concerned relate to internal control procedures for optimizing the performance of the dialysis system or the dialysis apparatus and not to a particular medical application of the dialysis apparatus for carrying out a treatment of a patient. This means that the mentioned machine control processes run automatically and independent of a patient's treatment for maintaining the internal machine function.

Furthermore, in the relevant prior art e.g. according to DE 699 16 053 T2 there is disclosed a further measurement method for the determination of waste products in machine-internal dialysis solutions during the dialysis treatment by use of a spectral-photometric measurement, in particular using UV light. To be more precise, this measurement method according to DE 699 16 053 T2 is based on the general principle of photometry, according to which a light source is used and so-called photosensors serve as detectors. In such an arrangement, the light source emits a light signal with a wavelength from 180 to 380 nm. This wavelength is absorbed by urinary excreted substances (uremic toxins).

All these known methods are capable of selectively determining the machine-specific effectiveness of the dialysis by identifying a recirculation in the shunt, but there are the following limitations:

The administration of the bolus is usually performed (except for the spectral-photometric measurement) on the blood side in the venous portion, with the requirement that the measurement has to be carried out after that likewise on the blood side in the arterial portion. Any disturbances between the measurement intervals remain concealed and cannot be identified. The selective blood-sided measurements have a negative impact on the treatment. As the measurements are carried out on the blood side and not on the side of the dialysis solution, they have to be performed and attended by suitable qualified staff.

SUMMARY OF THE INVENTION

In view of this problem, it is an object of the present invention to permit an online monitoring of the dialysis therapy or session and of the effectiveness of the dialysis and to perform the measurement in the circulation of the dialysis solution (dialysis solution side), i.e. exclusively internal to the machine and hence separated from the patient and thus separated from the treatment of the patient as such. Further, an aim of the invention shall be to base the measurement on the sensor technology which is generally present in the dialysis apparatus anyway.

This object is achieved with a measurement and determination method (internal to the machine and based on control technology) comprising the method steps according to claim 1 as well as by a device comprising the features according to claim 6. Advantageous configurations and/or further developments of the present invention are subject-matter of the sub-claims.

According to one aspect, the gist of the present invention is to provide a (control) method which is internal to the machine and serves, on the side of the dialysis solution, for detecting/determining a recirculation by/during a blood-sided administration of a bolus comprising at least one the following method steps or control process steps:

measuring a first (UV) light absorbance value (or absorption value) of a dialysis solution draining off a dialyzer, by means of a spectrometer, prior to the administration of the bolus;

venous administration of the bolus (e.g. NaCl or any other substance which shows no absorption or a heavy and known absorption at the light wavelength of 280 nm) having a predefined volume (adaptive determination on the base of the blood flow or fixed) at the venous access or immediately upstream thereof;

measuring a second (UV) light absorbance value (or absorption value) of the draining dialysis solution, by means of a spectrometer, after the administration of the bolus, preferably determining the period of time elapsed between measuring the first absorbance value (ad) and the second absorbance value (bd); and determining a change in the absorbance value (or a change in the absorption value) between the first and second measured absorbance values (or absorption values) caused by a (diluting) presence of a bolus in the dialysis solution due to recirculation possibly as a basis for a following quantification of the recirculation (i.e. the presence of a detected/determined absorbance difference (or absorption difference) in the dialysis solution due to the recirculation may then be used as the basis for a subsequent recirculation quantification).

This method allows to detect and possibly also quantify a change in the absorbance value (or a change in the absorption value) caused by the venous-administered bolus (predefined amount) in an easy way by using a UV sensor at the dialyzer outlet on the side of a dialysis solution for a defined period of time during the dialysis treatment. A recirculation effect is the only possibility by which this bolus administered to the vein is able to arrive at the dialyzer (partially) and results in a reduction of the concentration of measurable uremic toxins at this place; for that reason, this reduction of the concentration is an indirect measure for the recirculation degree at the time of measuring.

According to a further development of the present invention, the following method steps are provided in addition:

determining the integral of the altered absorbance (or absorption) curve for the first and second absorbance values (or absorption values) prior to and after the bolus, whereby two integral surface areas are calculated;

calculating the difference between the two integral values/the two integral surface areas prior to and after the bolus;

identifying a recirculation state (which is not quantified for the time being) if a difference (C) is unequal to zero.

In other words, the dialysis apparatus control method according to aspects of the invention relates in principle to 1) acquiring detector signals which are delivered by a usually present UV sensor in the dialysis solution portion of the dialysis apparatus prior to and after an administration of a bolus, e.g. NaCl or any other substance which has no absorption or a strong and known absorption at a light wavelength of 280 nm;

2) detecting a signal alteration (for instance by a reduction of the concentration of uric acid in the arterial access by the bolus); and preferably 3) determining the presence of a recirculation on the basis of the signal value difference determined from the signal alteration.

The above-mentioned control method step 3) is preferably subdivided into the following steps:

4) determining the integral over the signal curve prior to and after the bolus;

5) determining a difference between the two integral values for the signal curve prior to and after the bolus; and 6) identifying the presence of a recirculation if an integral value difference is unequal to zero.

These method steps offer the possibility to determine the presence of a recirculation in order to possibly initiate further method steps for its quantification (recirculation degree) later on. These further method steps may include the following steps:

converting the one integral value/the one integral surface area prior to the bolus administration as well as converting the difference between the integral values/integral surface areas by calculation into associated absorbance values;

calculating the arterial bolus quantity (corresponds to the bolus proportion which has wandered to the dialysis solution due to recirculation) from the ratio of the absorbance values which have been converted by calculation; and calculating the recirculation degree from the ratio between the calculated arterial bolus quantity and the predefined venous (added) bolus quantity.

This last method step allows for the quantification of a recirculation, if any, merely with the aid of at least one UV sensor.

According to another aspect of the present invention, there is provided a dialysis apparatus comprising a device for detecting a recirculation, on the side of a dialysis solution, by means of a blood-sided administration of a bolus by implementation of the method according to the above definition, comprising at least one light source which emits light with a wavelength from 250 to 300 nm and preferably of 280 nm, at least one UV sensor preferably directly at the drain (on the side of the dialysis solution) of a dialyzer, and an arithmetic unit which receives sensor signals regarding the UV absorbance (or UV absorption) of the dialysis solution prior to and after a blood-sided venous administration of the bolus from the at least one UV sensor and which preferably determines the integral over the signal curve for a defined period of time prior to and after the administration of the bolus.

The present invention also uses the measuring principle already known from DE 699 16 053 T2 as a measurement method according to the previous description. Here, the light source is an LED emitting light with a wavelength of approximately 280 nm, as has already been explained above, which in the present case is detected by two photo detectors (UV sensors). At least one sensor is situated in the drain (directly) behind the dialyzer of the dialysis apparatus on the side of the dialysis solution and measures the absorbance (or absorption) in the effluent dialysis solution during the dialysis in continuous or clocked manner.

The method according to aspects of the invention allows an online monitoring of the therapy and the effectiveness of the dialysis, with the measurement not occurring on the patient but on the side of the machine in the circulation of the dialysis solution. Further, the measurement is based (exclusively) on the sensor technology which is already present in the dialysis apparatus.

BRIEF DESCRIPTION OF THE DRAWINGS

The invention is best understood from the following detailed description when read in connection with the accompanying drawings. Include in the drawings are the following figures.

DETAILED DESCRIPTION OF THE PREFERRED EMBODIMENTS

Figure 1:
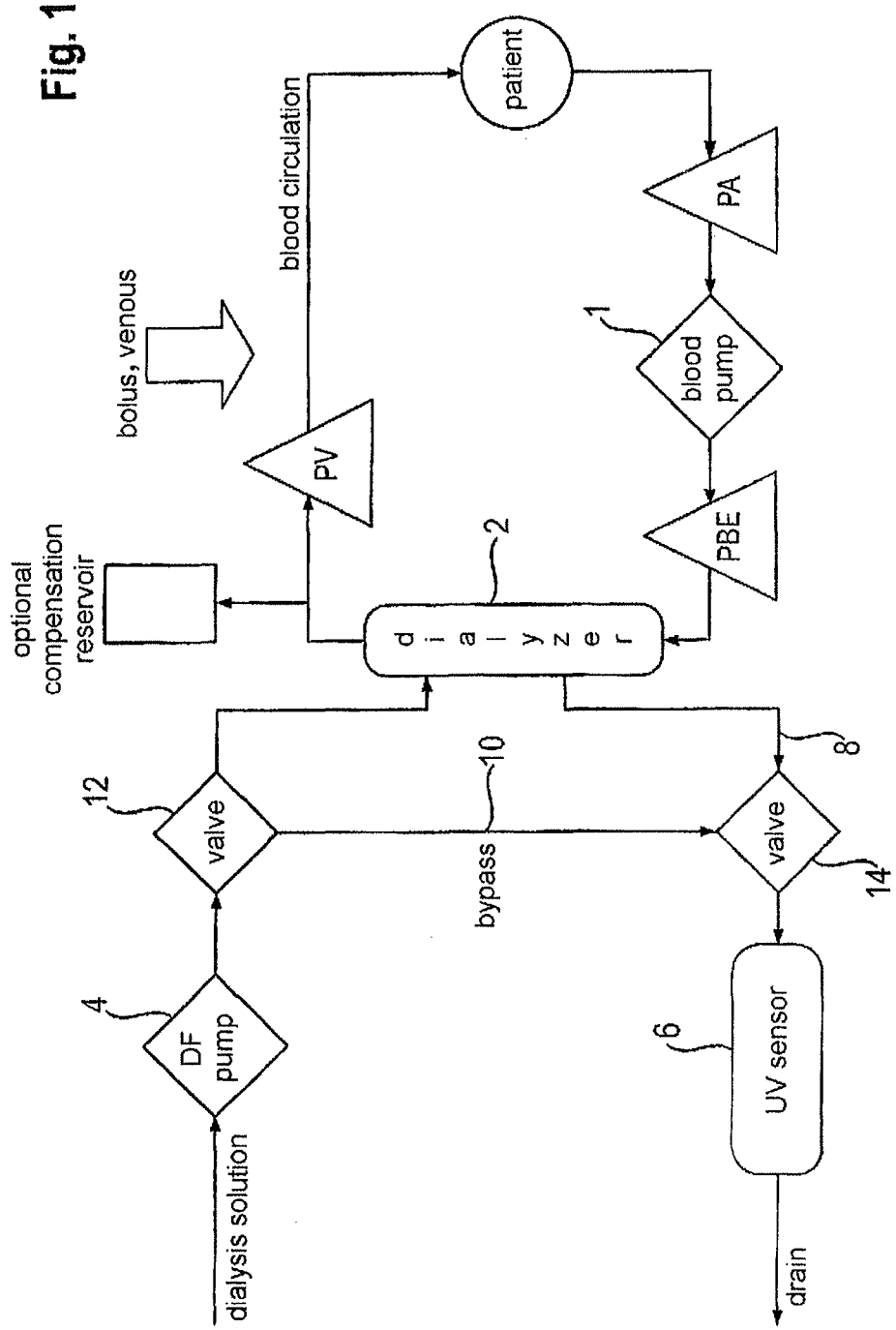
FIG. 1 shows the basic design and the flow conditions in a dialysis apparatus according to aspects of the invention without recirculation.

FIG. 1 illustrates the basic design of a dialysis apparatus (flow of the dialysis solution) without recirculation according to the present invention. Accordingly, a blood pump 1 conveys blood from the body of a patient via pressure measuring devices (not specified in more detail below) into a dialyzer 2 which receives a dialysis solution at its machine side pumped in countercurrent with respect to the blood by means of a dialysis solution pump 4. The blood and the dialysis solution are separated from each other by a semi-permeable membrane (not shown in more detail) which is permeable for uremic toxins in the direction toward the dialysis solution. The dialysis solution enriched with uremic toxins will then be discharged from the dialyzer 2.

At least one UV sensor 6 is provided in/on a discharge line 8 downstream of the dialyzer 2 and continuously measures the (UV light) absorbance in the drain (dialysis solution) during a dialysis therapy. At the beginning and for the purpose of calibrating the system (sensor technology), a detector 0 value is determined with a pure dialysis solution (without any uremic toxins), in fact preferably at a time at which the patient is not yet connected to the dialysis apparatus or at which the dialyzer 2 is bypassed via a bypass line 10 which can be provided with a fluid connection to the input and output of the dialyzer 2 at two valves 12, 14. In the latter case (bypass solution), the UV sensor 6 is arranged downstream of the bypass line 19 at the dialyzer drain 8. Subsequently, the dialysis solution will again be sent through the dialyzer 2 and measured by the UV sensor in continuous or clocked fashion. The sensor signals generated in this process (detector i) will be supplied to an arithmetic unit (not illustrated in further detail) which determines from these signals the current (UV light) absorbance value as follows:

$$A = \log_{10}\left(\frac{\text{detector}_0}{\text{detector}_i}\right)$$

As already explained above, the detector 0 value is the level calibrated at the beginning of the dialysis treatment, which is carried out with a dialysis solution free from the substances to be measured. The flow of the dialysis solution, the blood flow and the employed dialyzer 2 have influence on the absorbance and hence on the prevailing clearance (proportion of the blood flow in relation to the total blood flow which is completely purified from uremic toxins), which is crucial for the (UV light) absorbance in the drain. In this process, the extracted poisonous substances from the blood side are diluted by the flow of the dialysis solution and then measured in the drain by the at least one UV sensor 6.

As already described at the outset, already cleaned blood from the venous access will be drawn back into the arterial access during a recirculation in the shunt. Here, the recirculation (in %) is the ratio between the cleaned blood and the current blood flow. This means that not the actual, currently existing concentration of poisonous substances in the patient is transported to the dialyzer 2, but only a dilution with already cleaned blood, which is why the effectiveness of the dialysis is reduced, of course.

Figure 2:
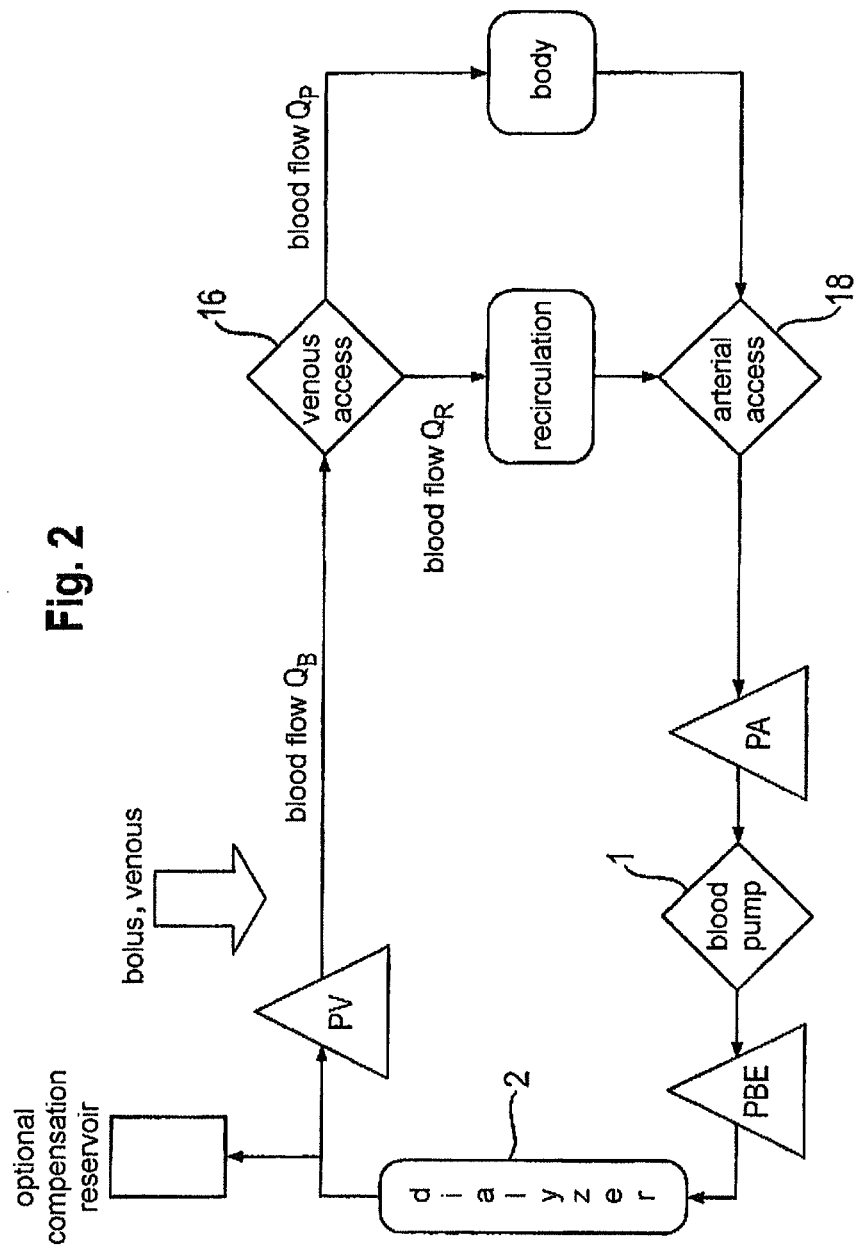
FIG. 2 shows the basic design and the flow conditions in a dialysis apparatus according to aspects of the invention with recirculation.

FIG. 2 shows the principle of the dialysis apparatus according to aspects of the invention in a recirculation state. Accordingly, cleaned blood is discharged into the venous access 16; immediately thereafter, it is again drawn into the arterial access 18 parallel to the arterial blood of the patient. In this process, the blood flow which is indicated in FIG. 2 as being parallel to the patient's body constitutes the recirculation.

It may be calculated from:

$$\text{recirculation } R\, [\%] = \frac{Q_R}{Q_B}$$

$$Q_B = Q_R + Q_P$$

where QB=total blood flow
QR=recirculation blood flow
QP=patient's blood flow

Starting from the previous basic considerations, the absolute recirculation can be determined in the manner described below:

A triggered measurement for determining an absolute recirculation in a shunt is carried out according to aspects of the invention by the administration of a bolus into the venous access. This method can also be (continuously) carried out during a recirculation which does not occur suddenly, and determines/calculates the absolute value of the recirculation.

The administration of the bolus into the venous, extracorporeal circulation can take place first in various ways by syringes, back-filtration, substitution pumps etc. and has to be added only (directly) upstream the venous access. The bolus itself should preferably consist of a non-absorbing substance (e.g. NaCl). If the concentration of the bolus is known and this concentration is also calibrated to the UV sensor, it is alternatively possible to work with an absorbing bolus substance, too.

Basically, a specific bolus quantity (volume) QBven of e.g. 10 ml NaCl is administered to the patient via the vein. To this end, the amount of the bolus may be adaptively adjusted to the blood flow and hence can be optimally calculated or can be defined by a fixed amount. The administration of the bolus is performed preferably when the blood flow is stopped, with the option that a bolus administration may also occur parallel to the flowing blood flow.

Figure 3:
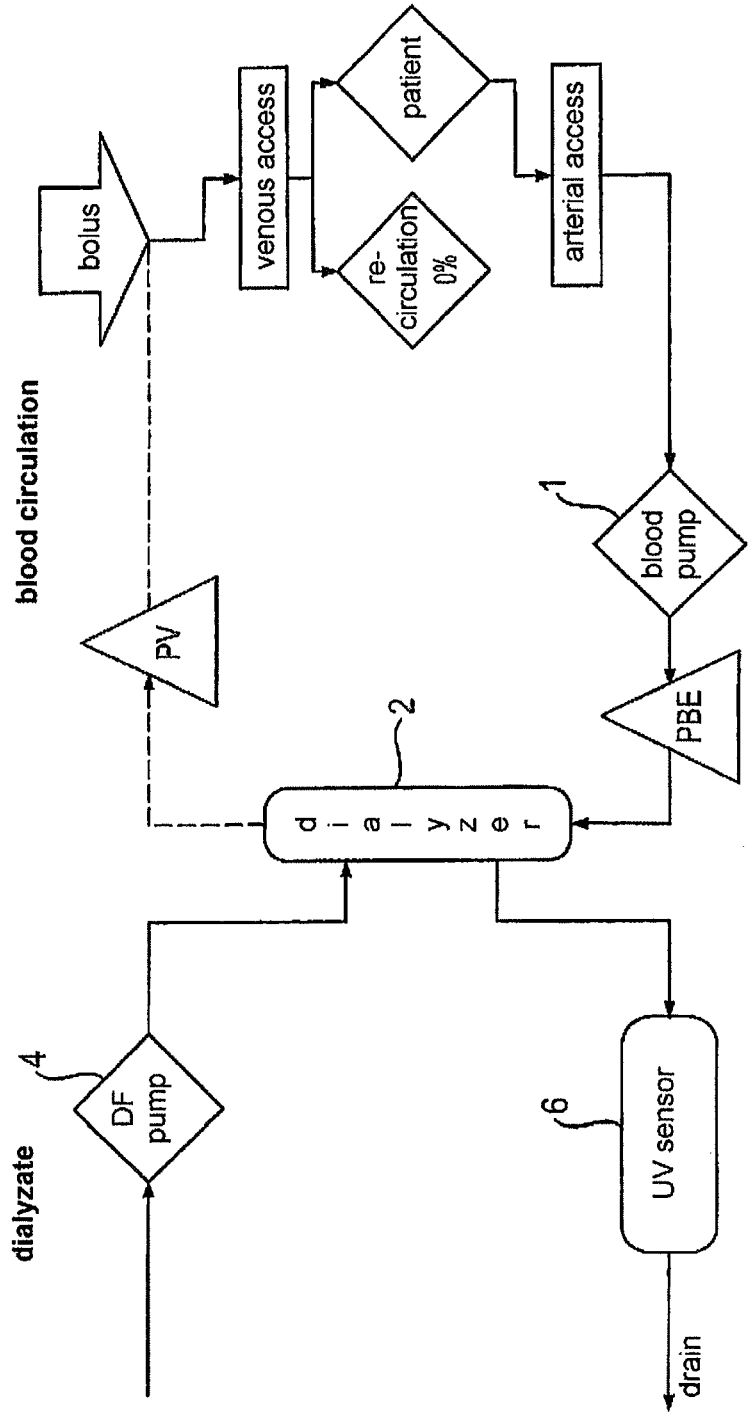
FIG. 3 shows the blood circulation in the shunt area without recirculation during bolus administration.
Figure 4:
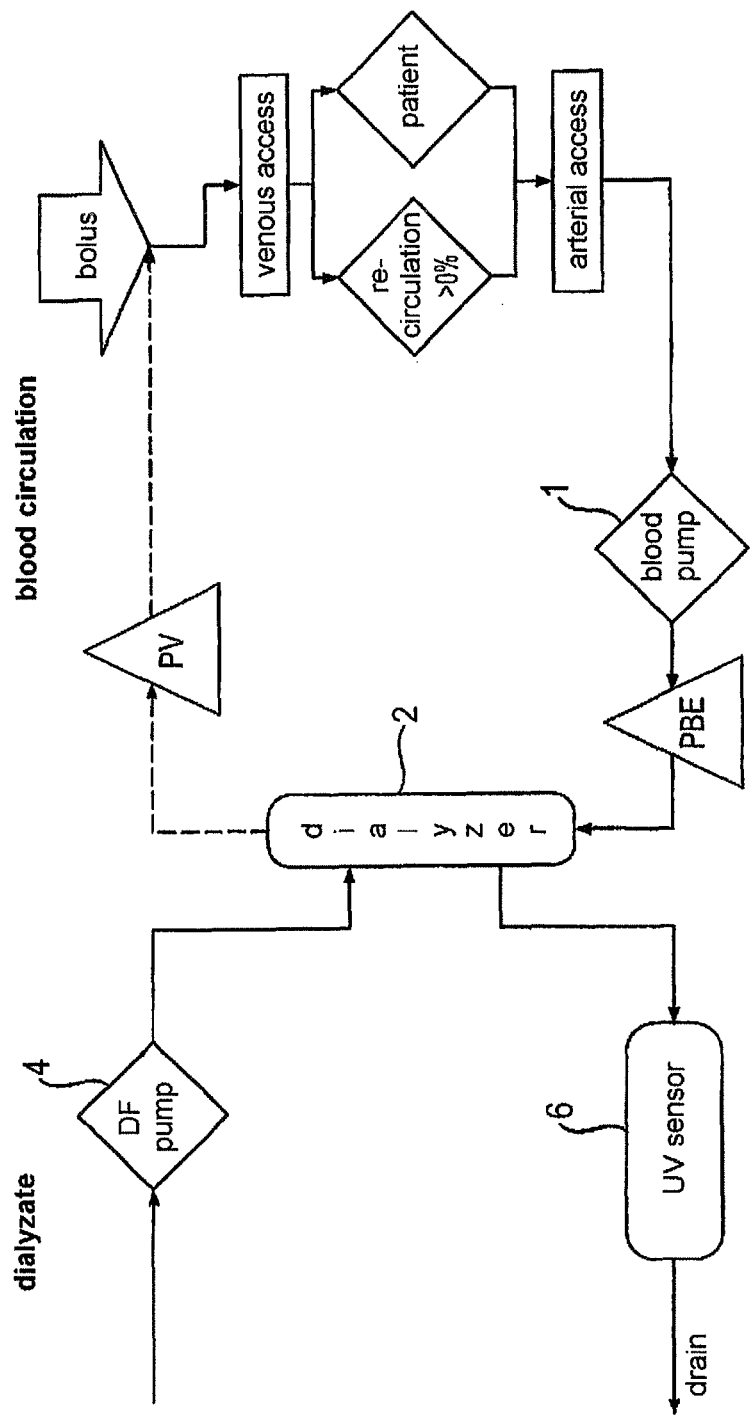
FIG. 4 shows the blood circulation in the shunt area with recirculation during bolus administration and FIG. 5 depicts the qualitative course of a UV sensor signal during venous bolus administration at the shunt and with recirculation.

FIGS. 3 and 4 show the behavior of the system with and without recirculation for a bolus according to the above definition. FIG. 3 shows the behavior where there is no recirculation, whereas FIG. 4 illustrates the behavior with recirculation and the diluted liquid in the arterial access. Correspondingly, the bolus according to FIG. 3 flows via the venous access exclusively into the patient's body and from there (in a concentration which is not perceptible any more) into the arterial access. In this arterial access, the UV sensor does not detect any alteration of the absorbance value immediately after the administration of the bolus.

The system according to FIG. 4 shows a different behavior. Here, the bolus does not flow exclusively into the patient's body, but in proportioned manner also directly into the arterial access. This results in a quick reduction of the absorbance value measured on the side of the dialysis solution compared to the value which prevailed in the time before the administration of the bolus, due to the recirculation being larger than zero (%).

In other words, if there is no recirculation in the shunt, there will be no signal alteration prior to and after the bolus administration regarding the absorbance or the UV sensor signal, as only uncleaned blood is received by the arterial access, whereas the bolus is distributed/dissipated in the patient's body. A recirculation in the shunt (see FIG. 4), however, causes a direct signal alteration at the UV sensor due to a reduction of the concentration of uremic toxins (uric acid concentration) in the arterial access and hence in the dialysis solution. In this process, already cleaned blood and also the bolus from the venous access will again be directly received by the arterial access (without flowing through the patient's body) and are conveyed past the dialyzer. This results in a smaller removed amount of uremic toxins and hence in a lower concentration of uric acid (abrupt concentration transition) in the effluent dialysis solution.

Figure 5:
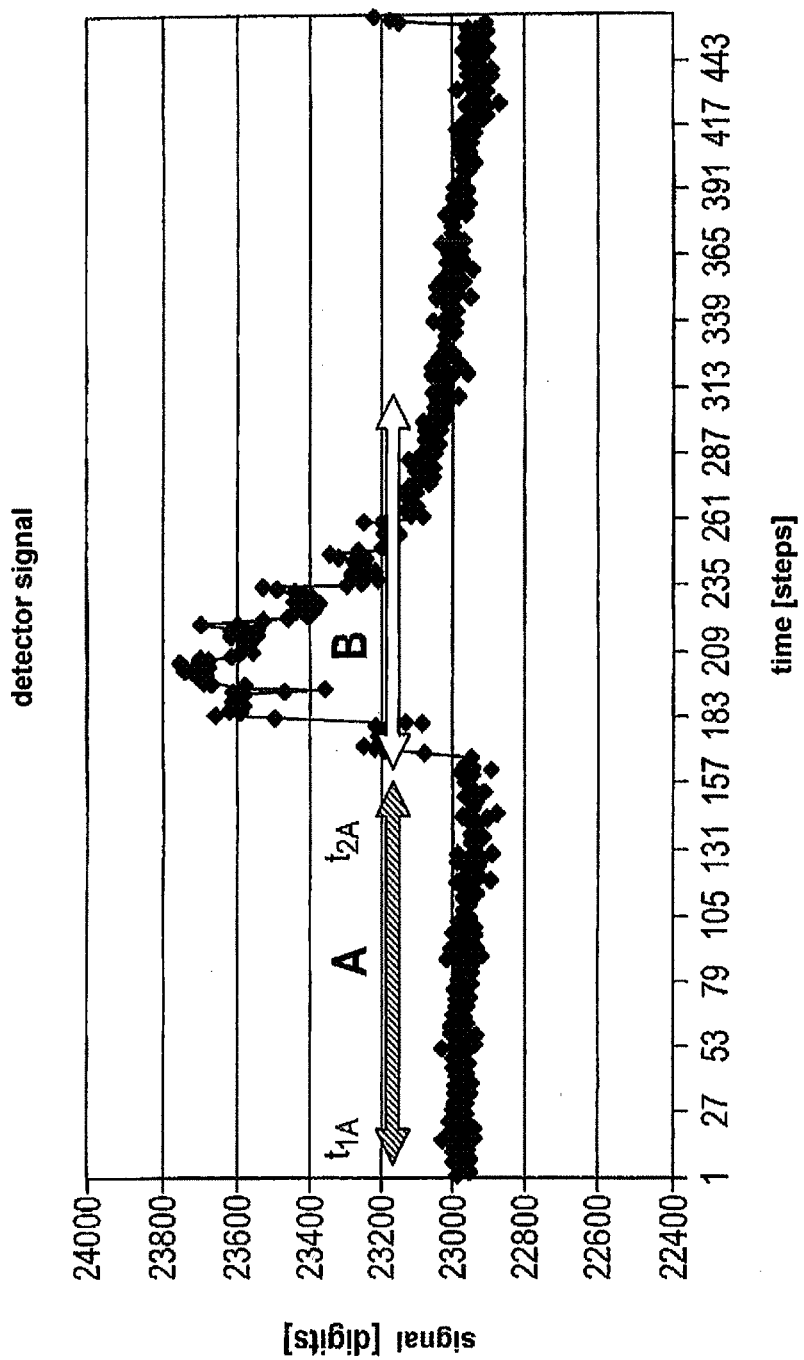

A qualitative signal curve at the UV sensor in the case of a bolus administration with recirculation is illustrated in FIG. 5. Accordingly, the detection signal prior to the bolus administration shows a substantially constant course, and then exhibits an abrupt signal step directly after the bolus administration, indicating a substantially abrupt alteration of the concentration of uremic toxins in the dialysis solution. As soon as the bolus has passed the dialyzer, the sensor signal gradually returns to its value prior to the bolus administration.

The determination of the integral over the signal curve for a specific period of time prior to and after the bolus administration forms the basis for the quantitative signal evaluation by the arithmetic unit which is not illustrated in further detail. The measured quantity for the detection of the recirculation with the illustrated UV sensor is thus (solely) the detector signal changing due to being controlled only with the concentration of uric acid and hence with the proportional absorbance in the dialysis solution.

In order to measure/calculate the precise recirculation degree, the calculation must be carried out by way of the absorbance, as the latter is directly proportional to the concentration. According to FIG. 4, the added bolus arrives at the venous access in mixed/diluted form and serves as a starting substance for the determination of the recirculation. With the help of the two aforementioned integral surface areas A, B according to the FIG. 5, it is now possible to calculate/determine the recirculation degree (in quantitative manner).

The surface area A reflects the stationary value which has leveled off in the dialysis solution without any influence by the bolus. The bolus changes said system and, for a short time, the concentration. This change can now be determined via the ratios of the absorbance values. The prerequisite, however, is the knowledge of the volume QBven of the bolus which has been delivered to the venous access.

The calculation is then carried out by determining the integral surface areas A, B. The measuring length of the integral surface areas does not necessarily have to be equal in length. For different lengths, however, the bolus quantity must be calculated by the measuring length. The difference of the two integral surface areas $$C=B-A$$

results in the differential surface area C. The latter is the result of adding the bolus and is directly proportional to the bolus (recirculated amount). If A=B, this means that there is no measurable recirculation in the system. The knowledge of the amount QBven of the added bolus allows for calculation of the recirculation. This is the ratio between the amount of the added venous bolus QBven and the (recirculated) part QBart received therefrom by the artery.

$$\text{Recirculation}=QBart/QBven=QR/QB$$

The arterial bolus quantity QBart is that bolus quantity in ml which corresponds to the proportion in the arterial access by recirculation. The determination is made by calculating the ratios between the integral surface areas A, B and the real blood flow.

The surface areas A to C are calculated from the detector signal. The adaptation is performed for instance by a Gaussian function of 7th order or another applicable mathematic function for determining a surface area.

$$\text{surface area\_C} = \int_{t_1}^{t_2} \left( \sum_1^7 \left( a_i \cdot e^{-\left(\frac{x_i-b_i}{c_i}\right)^2} \right) \right)$$

The calculation of a C detector value and of an A detector value of the respective surface areas C and A is further carried out by averaging the respective surface area throughout the defined measuring period. In this way, the real surface area is calculated and it is possible to calculate (via the surface areas)

the change in the mixing ratio (dialysis solution/uremic toxins) in the dialysis solution by the calculation of the absorbance.

That is, the respective surface area is converted into the absorbance by calculation and hence is proportional to the concentration. A point-to-point comparison is also possible, but has a lower measuring accuracy. Basically, the absorbance is calculated from:

(Detector 0=55000 is exemplarily used as the initial level having a pure dialysis solution)

Absorbance$(A,B,C)$=log 10(detector0/detector value (real))

Bolus quantity(arterial)=1−(absorbance$(C)$/absorbance$(A)$)*(blood flow*measuring period)

The overall determination of the absolute recirculation will then be carried out with the following calculation formula:

$$\text{recirculation} = \left( \frac{\left(1 - \left(\frac{\log_{10}\left(\frac{\text{detector}_0}{\text{detector value}_B}\right)}{\log_{10}\left(\frac{\text{detector}_0}{\text{detector value}_A}\right)}\right)\right) \cdot (\text{blood flow} \cdot (t_{2b} - t_{1b}))}{\text{bolus quantity\_venous}} \right)$$

In summary, a method and a device implementing this method are disclosed, intended for the detection of a recirculation, on the side of a dialysis solution, by a blood-sided administration of a bolus, comprising the following method steps:
  measuring a first light absorbance value (ad) of a dialysis solution (d) draining off a dialyzer, by means of a spectrometer, prior to the administration of the bolus;
  venous administration of the bolus having a predefined volume (QBven) at the venous access;
  measuring a second light absorbance value (bd) of the draining dialysis solution, by means of a spectrometer, after the administration of the bolus; and
  determining a change in the absorbance value (absorbance difference) between the first (ad) and second (bd) measured absorbance values due to the presence of a bolus in the dialysis solution during recirculation as a basis for an optional recirculation quantification.

The invention claimed is:

1. A method of detecting a recirculation, at the side of a dialysis solution, by means of a blood-sided administration of a bolus, comprising the following method steps:
  emitting light having a wavelength from 250 to 300 nm with a light source;
  positioning at least one UV sensor at a drain of a dialyzer;
  measuring a first light absorbance value (ad) of a dialysis solution (d) draining off a dialyzer, with a spectrometer, prior to the administration of the bolus;
  administering the bolus having a predefined volume (QBven) at the venous access;
  measuring a second light absorbance value (bd) of the draining dialysis solution with the spectrometer, after the administration of the bolus;
  receiving, with an arithmetic unit, sensor signals from the spectrometer regarding UV absorbance of the dialysis solution prior to and after the administration of the bolus;
  determining, with the arithmetic unit, a change in the absorbance value between the first (ad) and second (bd) measured absorbance values due to the presence of the bolus in the dialysis solution (d) during recirculation as a basis for the recirculation quantification;
  determining, with the arithmetic unit, an integral value (A) of an altered absorbance curve for the first absorbance value (ad) prior to the bolus administration;
  determining, with the arithmetic unit, an integral value (B) of an altered absorbance curve for the second absorbance value (bd) after the bolus administration;
  calculating, with the arithmetic unit, a difference between the two integral values (A, B) prior to and after the bolus;
  identifying, with the arithmetic unit, a recirculation state if a difference (C) between the two integral values is unequal to zero;
  converting, with the arithmetic unit, the integral value (A) and the integral value difference (C) into associated absorbance values (AA, CA) by calculation;
  calculating, with the arithmetic unit, an arterial bolus quantity (QBart) from the ratio of the absorbance values (AA, CA); and
  calculating, with the arithmetic unit, a recirculation degree from the ratio between the calculated arterial bolus quantity (QBart) and the predefined volume (QBven).

2. The method according to claim 1, wherein the bolus does not have any absorbance characteristics with respect to the light emitted into the dialysis solution.

3. The method according to claim 1, wherein the bolus has predefined absorbance characteristics with respect to the light emitted into the dialysis solution in terms of the uremic toxins in the dialysis solution.

4. A dialysis apparatus comprising:
  a light source which emits light with a wavelength from 250 to 300 nm;
  at least one UV sensor positioned at a drain of a dialyzer;
  a spectrometer configured to:
    measure a first light absorbance value (ad) of a dialysis solution (d) draining off of a dialyzer prior to administration of a bolus, and
    measure a second light absorbance value (bd) of the dialysis solution (d) draining off of the dialyzer after administration of the bolus; and
  an arithmetic unit configured to:
    receive sensor signals from the spectrometer regarding UV absorbance of the dialysis solution prior to and after a blood-sided venous administration of the bolus having a predefined volume (QBven) at a venous access;
    determine a change in absorbance value between the first (ad) and the second (bd) measured absorbance values due to the presence of the bolus in the dialysis solution (d) during recirculation as a basis for recirculation quantification;
    determine an integral value (A) of an altered absorbance curve for the first absorbance value (ad) prior to the bolus administration;
    determine an integral value (B) of an altered absorbance curve for the second absorbance value (bd) after the bolus administration;
    calculate a difference between the two integral values (A, B) prior to and after the bolus;
    identify a recirculation state if a difference (C) between the two integral values is unequal to zero;
    convert the integral value (A) and the integral value difference (C) into associated absorbance values (AA, CA) by calculation;
    calculate an arterial bolus quantity (QBart) from the ratio of the absorbance values (AA, CA); and calculate a recirculation degree from the ratio between the calculated arterial bolus quantity (QBart) and the predefined volume (QBven).

5. The dialysis apparatus of claim 4, wherein the wavelength is 280 nm.

6. The dialysis apparatus of claim 4, wherein the bolus does not have any absorbance characteristics with respect to the light emitted into the dialysis solution.

7. The dialysis apparatus of claim 4, wherein the bolus has predefined absorbance characteristics with respect to light emitted into the dialysis solution in terms of uremic toxins in the dialysis solution.

* * * * *